United States Patent
Hansen et al.

(10) Patent No.: US 6,347,631 B1
(45) Date of Patent: *Feb. 19, 2002

(54) CANTILEVER DEVICE AND METHOD FOR BREATHING DEVICES AND THE LIKE

(75) Inventors: Gary L. Hansen, Eden Prairie; Steven S. Bordewick, Shoreview, both of MN (US); Nicole Denise Bloom, San Francisco, CA (US)

(73) Assignee: Mallinckrodt, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/436,406

(22) Filed: Nov. 9, 1999

(51) Int. Cl.[7] ............................................. A62B 18/08
(52) U.S. Cl. .............................. 128/207.11; 128/207.13
(58) Field of Search ...................... 128/206.27, 207.11, 128/207.13, 207.17, 207.18, DIG. 26

(56) References Cited

U.S. PATENT DOCUMENTS

| | | | | |
|---|---|---|---|---|
| 1,081,745 A | * | 12/1913 | Johnston | 128/207.13 |
| 1,282,527 A | * | 10/1918 | Bidonde | 128/207.18 |
| 3,040,741 A | * | 6/1962 | Carolan | 128/207.11 |
| 3,752,157 A | * | 8/1973 | Malmin | 128/207.11 |
| 3,850,168 A | * | 11/1974 | Ferguson et al. | 128/206.27 |
| 4,080,664 A | * | 3/1978 | Morris et al. | 128/207.11 |
| 4,373,523 A | * | 2/1983 | Treutelaar | 128/207.18 |
| H397 H | | 1/1988 | Stark | 128/206.24 |
| 4,782,832 A | | 11/1988 | Trimble et al. | 128/207.18 |
| 5,421,799 A | | 6/1995 | Rabin et al. | 601/71 |
| D368,141 S | | 3/1996 | Rabin et al. | D24/215 |
| 5,611,771 A | | 3/1997 | Taylor | 601/70 |
| 5,763,030 A | | 6/1998 | Matsui | 428/35.7 |
| 5,767,634 A | | 6/1998 | Taylor et al. | 318/34 |
| D405,538 S | | 2/1999 | Chih | D24/215 |
| 6,044,844 A | * | 4/2000 | Kwok et al. | 128/206.27 |
| 6,119,694 A | * | 9/2000 | Correa et al. | 128/207.13 |

FOREIGN PATENT DOCUMENTS

| | | | | |
|---|---|---|---|---|
| DE | 186290 | * | 6/1907 | 128/207.11 |
| DE | 659476 | * | 5/1938 | 128/206.27 |
| EP | 0549299 | | 6/1993 | |
| FR | 385538 | * | 3/1908 | 128/207.11 |
| FR | 2517545 | | 6/1983 | |
| WO | 9804310 | | 2/1998 | |
| WO | 9824499 | | 6/1998 | |
| WO | 9848878 | | 11/1998 | |

OTHER PUBLICATIONS

Updated "Skalpi" advertisement, www.skymall.com.

* cited by examiner

*Primary Examiner*—Aaron J. Lewis
(74) *Attorney, Agent, or Firm*—Rothwell, Figg, Ernst & Manbeck

(57) ABSTRACT

A device for positioning a breathing apparatus over a breathing orifice in the head of a person, the person having an occipital lobe and an axis of symmetry, includes an occipital anchor for anchoring against the head of the person beneath the occipital lobe of the person. The device further includes a forward anchor for anchoring against a forward portion of the person's head. A spring connector connects the forward anchor and the occipital anchor, and biases the occipital anchor against the head of the person beneath the occipital lobe and the forward anchor against the corresponding portion of the person's head so as to attach the device to the person's head. The occipital anchor, the forward anchor and the spring connector are substantially aligned along the axis of symmetry of the person's head. The mount is connected to the spring connector for mounting the apparatus so as to locate the apparatus over the orifice.

20 Claims, 4 Drawing Sheets

CANTILEVER DEVICE AND METHOD FOR BREATHING DEVICES AND THE LIKE

BACKGROUND OF THE INVENTION

1. Field of the Invention

The present invention relates to the field of devices and methods for holding breathing devices and the like in place on a person's head.

2. Description of the Background Art

Breathing devices, such as masks and the like, typically are held in place on a person's face by a harness including one or more straps extending around the person's head and along the side of the person's face.

Known devices have a variety of drawbacks. If the strap system is complex, it may not be obvious to the prospective wearer how to properly use the system, and elderly patients may struggle with putting on a mask when help is not present.

A strap system which is incorrectly adjusted may result in improper positioning of the mask or excessive pressure to the skin.

Also, straps may contact sensitive regions of the face, resulting in abrasions or contact dermatitis over time. Additionally, straps may obscure portions of the face, causing distress to the wearer from a personal and aesthetic point of view. This can contribute to lack of compliance with wearing of the mask.

There remains a need in the art for improved methods and devices for positioning breathing devices and the like on a person's head.

SUMMARY OF THE INVENTION

In accordance with the present invention, a device is provided for positioning a breathing apparatus in communication with (i.e., over or within) a breathing orifice in the head of a person, the head of the person having an occipital lobe and an axis of symmetry. The device comprises an occipital anchor structure for anchoring against the head of the person about (i.e., beneath or against) the occipital lobe of the person, a forward anchor member for anchoring against a corresponding portion of the person's head at a forward anchoring position selected from the group consisting of a first portion of the persons head proximally surrounding said orifice (such as an area surrounding the nose and/or mouth, including the bridge of the nose) and a region located from the top portion of the person's head to the forehead portion of the person's head, and a biasing structure (such as a spring, array of springs, or other biasing member) connecting the forward anchor and the occipital anchor. The biasing structure biases the occipital anchor against the head of the person beneath the occipital lobe and biases the forward anchor against the corresponding portion of the person's head so as to attach the device to the person's head. The occipital anchor, the forward anchor and the biasing structure are substantially aligned along the axis of symmetry of the person's head. A mounting member also is connected to the biasing structure for mounting said apparatus so as to locate the apparatus over said orifice.

DETAILED DESCRIPTION OF THE INVENTION

The present invention provides a novel device and method for positioning an apparatus over a portion of a person's head. The invention generally is for positioning a head orifice-interacting apparatus over an orifice of the person's head.

The present invention is particularly applicable to devices to control sleep apnea, or to assist in breathing.

In preferred embodiments, the invention is for positioning a breathing device such as a breathing mask or respirator mask for covering at least one facial member selected from the group consisting of a person's nose, a person's mouth and a combination thereof. However, the invention can also be applied for positioning an apparatus over a person's ear or ears, such as a listening apparatus; or for positioning an apparatus over a person's eye or eyes such as a viewing apparatus. Additionally, the device can be utilized for positioning a speaking apparatus over a person's mouth, or any combination of the above.

In the embodiments shown in FIGS. 1–6, the device of the invention is provided for attaching a breathing mask over a person's nose, mouth or both.

Figure 1:
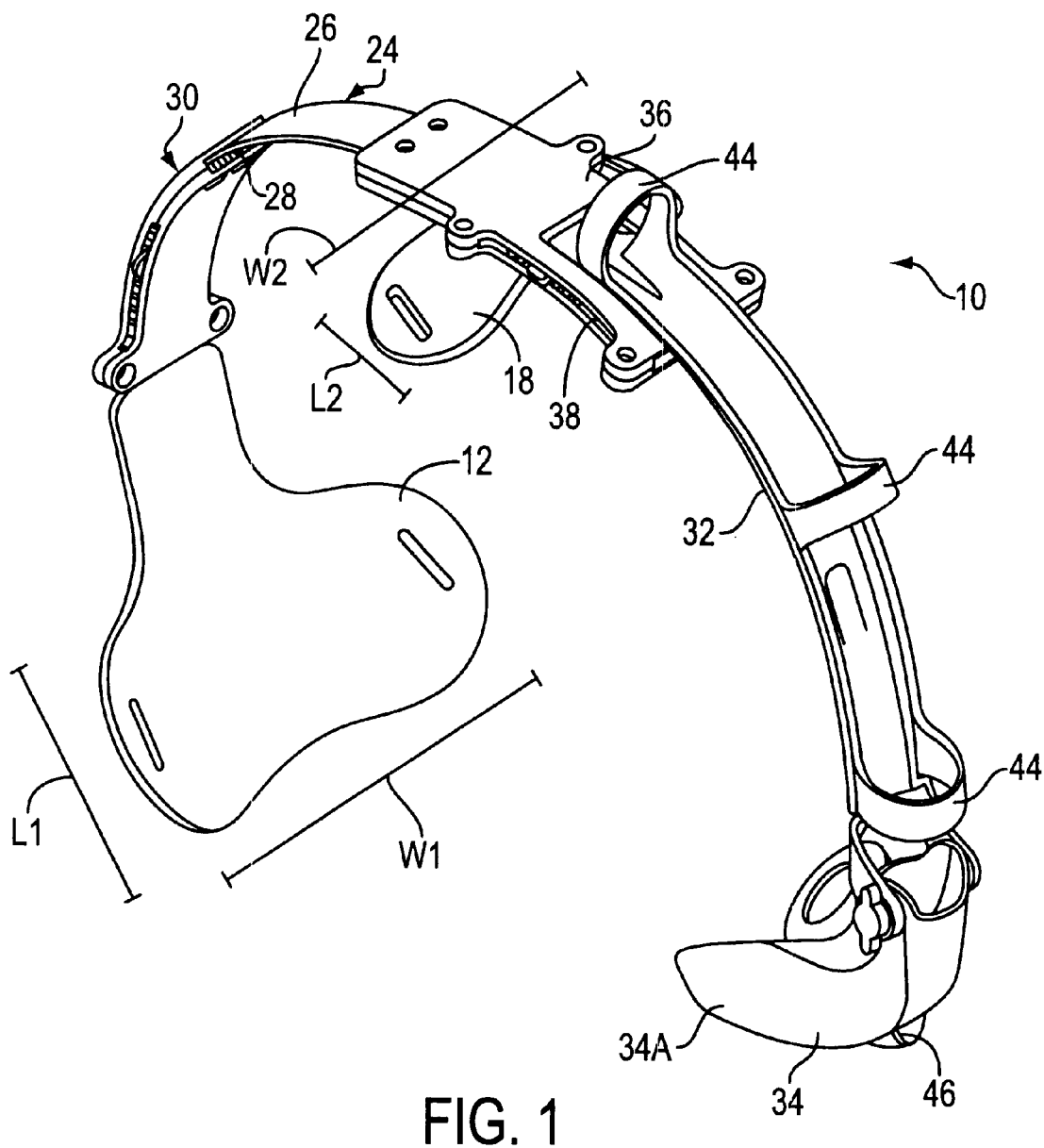
FIG. 1 is a perspective view of a device in accordance with one embodiment of the invention.
Figure 3:
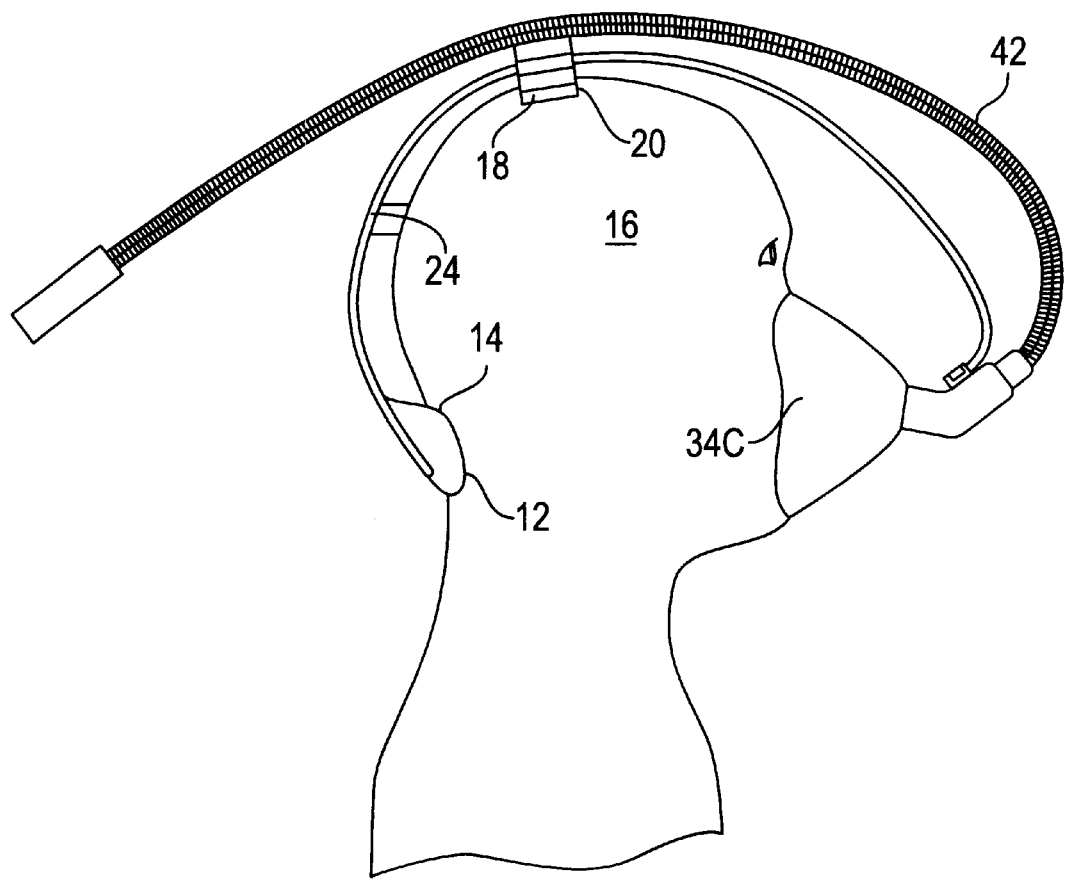
FIG. 3 is a side elevation view of a device in accordance with another embodiment of the invention.
Figure 4:
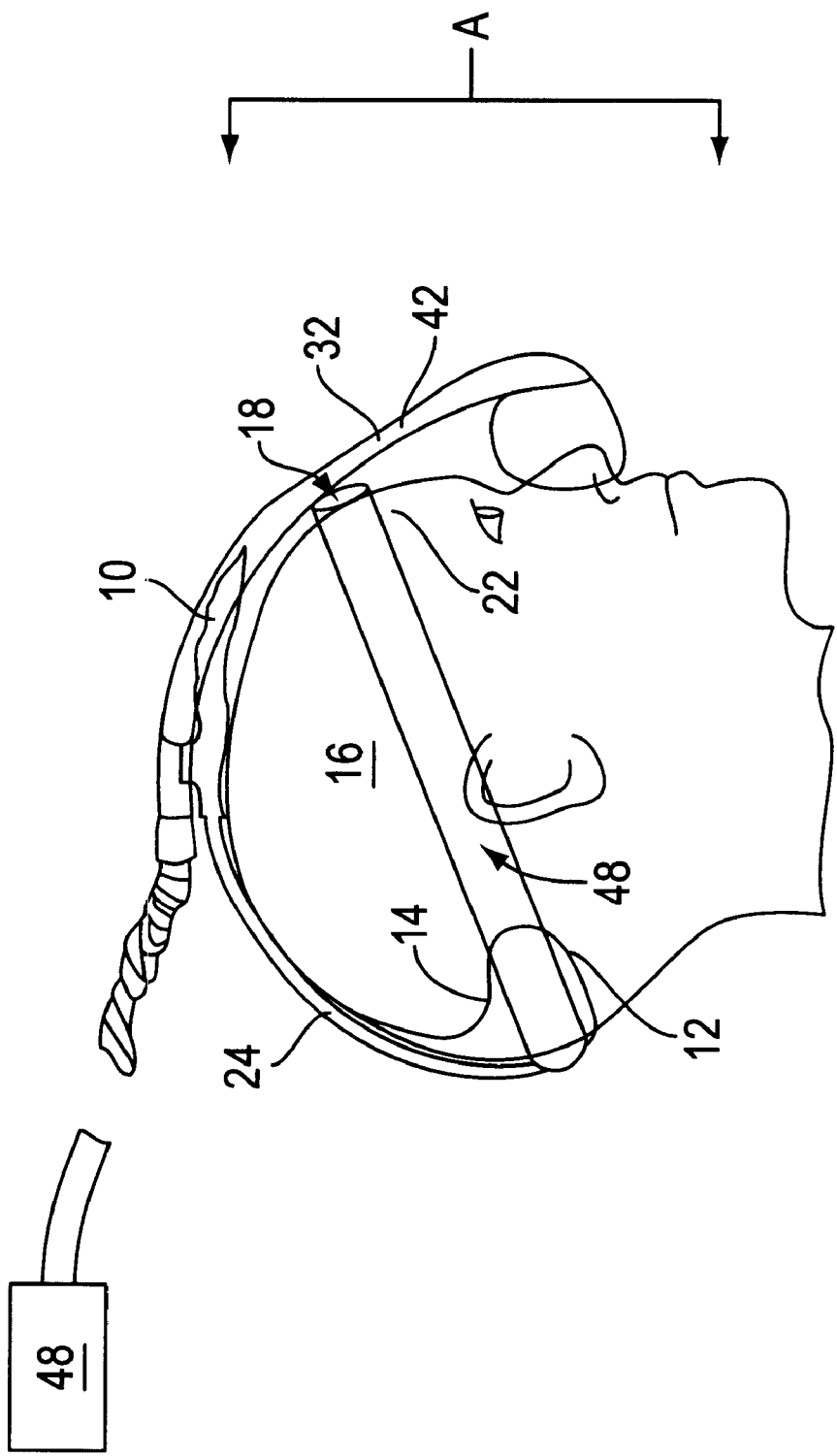
FIG. 4 is a schematic side elevational view of still another embodiment of the invention.

In the embodiment shown in FIG. 1, a device 10 in accordance with the present invention includes an occipital anchor 12 for anchoring against the portion of the person's head beneath the occipital lobe 14 of a person's head 16 shown in FIGS. 3 and 4. The occipital anchor 12 can have a length L1 within a range of about 2–8 centimeters, preferably about 3–7 centimeters, and a width WI within a range of about 5 to 20 centimeters, preferably about 8–12 centimeters.

Referring back to FIG. 1, the device 10 includes a forward anchor 18 for anchoring against a corresponding portion of the person's head selected from the group consisting of a top portion of the person's head 20 shown in FIG. 3, and a forehead portion 22 of a person's head shown in FIG. 4. As shown in FIG. 1, the forward anchor 18 can have a length L2 within a range of about 1 to 4 centimeters, preferably about 2 to 3 centimeters, and a width W2 within a range of about 5 to 11 centimeters, preferably about 7 to 9 centimeters.

The device 10 includes a biasing structure 24 connecting the forward anchor 18 and the occipital anchor 12. The biasing structure 24 biases the occipital anchor against the occipital lobe and the forward anchor against the top portion or the forehead portion of the person's head, so as to attach the device to the person's head.

The occipital anchor 12, the forward anchor 18 and the biasing structure 24 are substantially aligned along the axis A of symmetry of the person's head, which is in line with the plane of FIG. 4.

The biasing structure 24 extends between the occipital anchor 12 and the forward anchor 18 a distance within the range of about 7–30 centimeters, preferably about 10–18 centimeters. The biasing structure 24 can include a spring formed of spring steel, and as shown in FIG. 1, the distance between the occipital anchor 12 and the forward anchor 18 can be adjusted by spring 26 sliding within slot 28 of scabbard member 30.

Referring to FIG. 1, a mounting member 32 is connected to the biasing structure 24 for mounting a breathing mask 34, which in this case is a nostril mask 34A, to sealingly engage the nostril mask with a person's nostrils.

The mounting member 32 can extend between the forward anchor 18 and the breathing mask 34 a distance within the range of about 10 to 25 centimeters, preferably about 15 to 20 centimeters. As shown in FIG. 1, the device 10 has a second scabbard member 36 with a slot 38 within which the spring member 26 is slidable for adjustment of the device.

Figure 2:
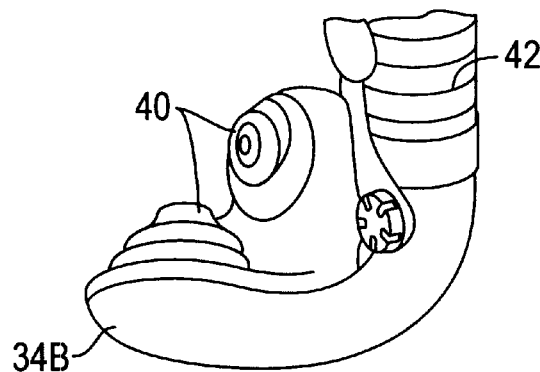
FIG. 2 shows details of a mask for use with the present invention including a pair of nostril-tubes for sealingly fitting within corresponding nostrils of a person's nose.

FIG. 2 shows a breathing mask 34B which is a Nasal Pillows™ type including a pair of nostril-tubes 40 for sealingly fitting within corresponding nostrils of a person's nose.

FIG. 3 shows a breathing mask 34C which sealingly covers both the patient's nose and mouth, the mounting member 32 being capable of biasing the breathing mask 34C so as to form a seal around the nose and mouth orifices.

In the embodiments shown, a gas plenum 42 is provided, as shown in FIGS. 2, 3 and 4. The embodiment shown in FIG. 1 shows structure for attaching a gas plenum to mounting member 32, including rings 44. The gas plenum is attached to the mounting member 32 and connectable to the breathing mask 34 for delivering gas to and from the breathing mask 34. Alternatively, the gas plenum can be formed as an integral part of mounting member 32.

The plenum 42 can have any suitable cross-sectional area, for example, within a range of about 100 to 500 mm$^2$. In particularly preferred embodiments, the gas plenum 42 is approximately 46 centimeters long and has a circular cross-section of 15 mm, with a cross-sectional area of about 175 mm$^2$.

In particularly preferred embodiments, the device 10 consists essentially of the occipital anchor 12, forward anchor 18, biasing structure 24 and mounting member 32, with the occipital anchor, forward anchor, biasing structure and mounting member being essentially the only means for attaching the breathing mask 34 to the person's head, the device being otherwise substantially free of any other means for securing the device to the person's head. In such embodiments, the device 10 is adapted to apply a force normal to the occipital anchor within a range of about 300–1,500 gm, with a preferred nominal force normal applied to the occipital anchor structure of about 800 gm. According to this embodiment, the preferred device is adapted to apply a force normal to the forward anchor 18 within a range of about 300 to 1,200 gm, with a nominal force normal applied to the forward anchor 18 of about 500 gm. The force normal applied to the breathing mask depends on whether the breathing mask is a Nasal Pillows™ (nostril-tube) type or a perimeter-type mask extending completely around the nose and mouth. For a Nasal Pillows™ type of mask, the goal is to minimize the force normal, whereas for a perimeter mask, a substantial force normal is required to make a sufficient air seal. Thus, a force normal applied to the breathing mask generally is within a range of about 0–1,000 gm, with a nominal force normal of about 100 gm being most preferred.

A device as shown in FIG. 1 preferably is adapted so that the lateral force necessary to cause side slippage on a person's head is within the range of about 200 to 500 gm, with a nominal lateral force necessary to cause side slippage of greater than about 300 gm.

Additionally, with a device as shown in FIG. 1, there is a force downward at the nose due to air pressure and structural loading through the air plenum within a range of about 0–300 gm, nominally about 100 gm.

For increased security and/or to provide greater fixation of the device, a side strap 48 can be provided as shown in FIG. 4, passing around the sides of the head and connecting the occipital anchor 12 with the mounting member 32. Side strap 48 preferably is formed of cloth or elastomeric material.

Figure 5:
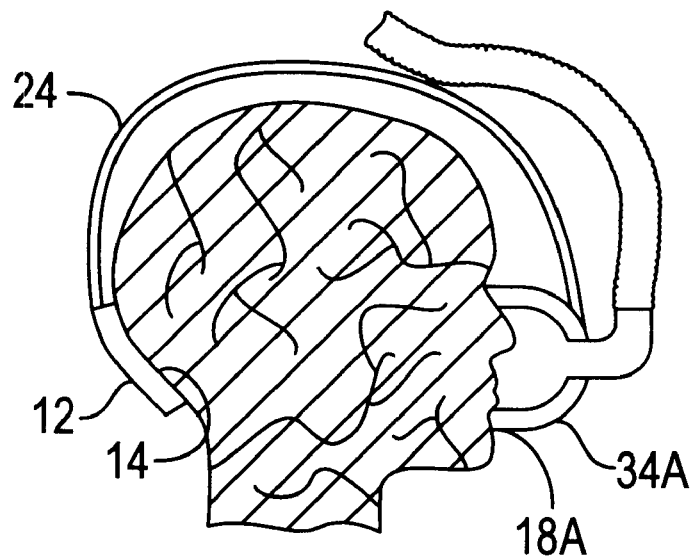
FIG. 5 is a schematic side elevational view of a further embodiment of the invention.
Figure 6:
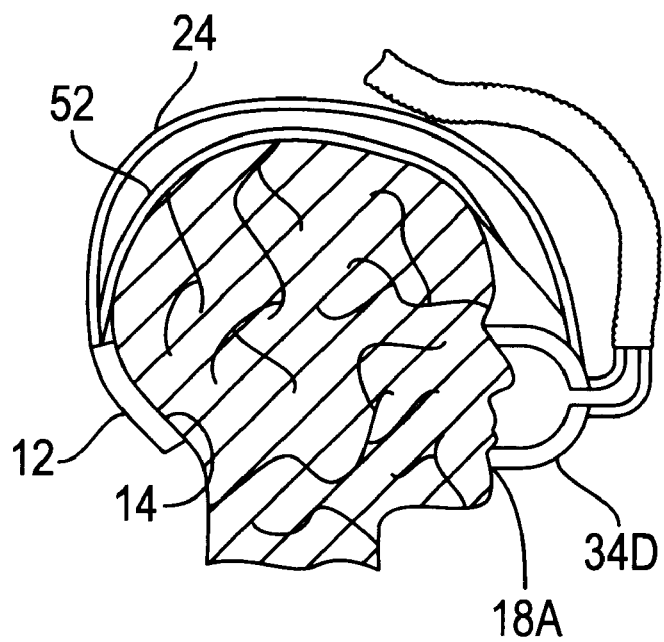
FIG. 6 is a schematic side elevational view of yet another embodiment of the invention.

FIGS. 5 and 6 show an embodiment where the forward anchor member 18A is comprised of the breathing apparatus such as mask 34D. In accordance with these embodiments, the spring force of biasing structure 24 holds the apparatus in place by pressure of face mask 34D against the front of the face and by pressure of occipital anchor 12 against the occipital lobe 14.

For increased security and/or to provide greater fixation of the device, a compliant sling 52 can be provided, having opposite ends connected to forward and rear portions of the biasing structure 24 as shown in FIG. 6. Sling 52 contacts the persons head when the breathing apparatus such as face mask 34D is located over the person's nose and/or mouth. Sling 52 provides frictional force at the top of the head, to aid in preventing the device from slipping sideways. The sling may be formed of any suitable compliant material such as fabric, plastic or the like, and may be elastic, inelastic or spring loaded. Sling 52 may also assist in rendering the device self-centering, wherein a perturbing lateral force is met by an opposing compensating force, so as to resist lateral slippage.

In the embodiment shown in FIG. 1, carbon dioxide-rich gas that the patient exhaled exits the system through vent 46 which is sized so that continuous positive airway pressure (CPAP) within the plenum flushes the hose and the plenum between breaths. A carbon dioxide vent is generally disclosed in U.S. Pat. No. 5,065,756, reissued as RE. 35,339, incorporated herein by reference.

The method of the present invention utilizing a device as shown in the figures includes the steps of positioning the occipital anchor against a person's occipital lobe, positioning the forward anchor against the corresponding portion of the person's head, and positioning the breathing mask over the person's nose, mouth or both, with the occipital anchor, the forward anchor and the biasing structure substantially aligned along the axis of symmetry of the person's head, and with the occipital anchor, forward anchor and breathing mask biased against the corresponding portions of the patient's head. When a CPAP system is utilized with the invention, the method of the invention includes the step of connecting the gas plenum 42 to a continuous source of respiratory gas 50, shown schematically in FIG. 4. In preferred embodiments, the method further includes the step of removing expired gas containing carbon dioxide from the gas plenum through vent 46 when the person exhales.

While many modifications, variations and changes in detail may be made to the described embodiments, it is intended that the matter in the foregoing description and shown in the accompanying drawings be interpreted as illustrative and not in a limiting sense.

What is claimed is:

1. A device for positioning a breathing apparatus over a breathing orifice in a person's head without the use of straps, the device consisting essentially of:

an occipital anchor adapted to fit against the head of a person about an occipital lobe of the person;

a forward anchor adapted to fit against a corresponding portion of a person's head at a forward anchoring position proximally surrounding a breathing orifice in the person's head;

a biasing structure connecting said forward anchor and said occipital anchor, said biasing structure adapted to bias said occipital anchor against a person's head beneath an occipital lobe and to bias said forward anchor against a corresponding portion of the person's head so as to attach the device to the person's head without the need for straps, wherein said occipital anchor, said forward anchor and said biasing structure are adapted to be substantially aligned along an axis of symmetry of the person's head; and a mounting member connected to said biasing structure for mounting the apparatus so as to locate the apparatus over a breathing orifice;

wherein said occipital anchor and said forward anchor are the only portions of said device adapted to contact the person's head.

2. The device of claim 1 wherein said mounting member is adapted to mount a breathing mask over an orifice present in at least one facial member selected from the group consisting of a person's nose, a person's mouth and a combination thereof.

3. The device of claim 2, wherein said mounting member is adapted to bias a breathing mask so as to form a seal around an orifice.

4. The device of claim 2 further comprising a gas plenum attached to said mounting member and connectable to the breathing mask for delivering gas to and from the breathing mask.

5. The device of claim 4, wherein said gas plenum has a cross-sectional area within a range of about 100 to 500 mm$^2$.

6. The device of claim 2 further comprising a breathing mask mounted on said mounting member.

7. The device of claim 6, wherein said breathing mask is adapted to cover a person's nose.

8. The device of claim 6 wherein said mask includes a pair of nostril-tubes for sealingly fitting within corresponding nostrils of the person's nose.

9. The device of claim 6, wherein in use, the device is adapted to apply a force normal to said breathing mask within a range of about 0–1,000 gm.

10. The device of claim 6, wherein said mask is a respiratory mask.

11. The device of claim 6, wherein said mask is adapted to cover a person's nose and mouth.

12. A method for attaching a breathing mask utilizing a device as a defined in claim 6 to a head of a person having an occipital lobe and axis of symmetry, the device consisting essentially of:

an occipital anchor for anchoring about the occipital lobe of the person;

a forward anchor for anchoring against a corresponding portion of the person's head at a forward anchoring position surrounding an orifice a biasing structure connecting the forward anchor and the occipital anchor, the biasing structure adapted to bias the occipital anchor against the occipital lobe and the forward anchor against the corresponding portion of the person's head so as to attach the device to the person's head without the use of straps, wherein the occipital anchor, the forward anchor and the biasing structure are substantially aligned along the axis of symmetry of the person's head; and a mounting member connected to the biasing structure and to a breathing mask for mounting the breathing mask so as to locate the breathing mask over at least one facial member selected from the group consisting of a person's nose, a person's mouth and a combination thereof;

the method comprising positioning the occipital anchor about the person's occipital lobe, and the forward anchor against the corresponding portion of the person's head, with the breathing mask in communication with at least one facial member of the person;

wherein the occipital anchor, the forward anchor and the biasing structure are substantially aligned along the axis of symmetry of the person's head, and wherein the occipital anchor is biased against the person's occipital lobe, the forward anchor is biased against the corresponding portion of the person's head, and the breathing mask forms a seal about the facial member, so as to attach the device to the person's head without the use of straps;

wherein said occipital anchor and said forward anchor are the only portions of said device adapted to contact the person's head.

13. The method of claim 12, wherein said device includes a gas plenum connected to the breathing mask, the method further comprising the step of connecting said gas plenum to a source of respiratory gas.

14. The method of claim 13 further including the step of removing expired gas containing carbon dioxide from said gas plenum after said person exhales.

15. The device of claim 2, wherein said occipital anchor has a length within a range of about 2 to 8 cm, and a width within a range of about 5 to 20 cm; said forward anchor has a length within a range of about 1 to 4 cm and a width within a range of about 5 to 11 cm; said biasing structure extends between said occipital anchor and said forward anchor a distance within a range of about 7 to 30 cm; and said mounting member extends between said forward anchor and said breathing mask a distance within a range of about 10 to 25 cm.

16. The device of claim 15, wherein said biasing structure has a length which is adjustable within said range.

17. The device of claim 2, wherein in use, the device is adapted to apply a force normal to said occipital anchor within a range of about 300 to 1,500 gm.

18. The device of claim 2 wherein in use, the device is adapted to apply a force normal to said forward anchor within a range of about 300 to 1,200 gm.

19. The device of claim 1, wherein said forward anchor member is comprised of a breathing apparatus.

20. The device of claim 19, further including a compliant sling having opposite ends connected to forward and rear portions of said biasing structure, for contacting the person's head when said apparatus is located over an orifice.

* * * * *